(12) United States Patent
Itonaga et al.

(10) Patent No.: US 6,565,524 B1
(45) Date of Patent: May 20, 2003

(54) COMPRESSION DEVICE FOR LIVING BEING

(75) Inventors: Kazunobu Itonaga, Kyoto (JP); Takahide Tanaka, Kyoto (JP); Yoshihiko Sano, Kyoto (JP); Hiroyuki Kato, Kyoto (JP); Hironori Sato, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 09/669,851

(22) Filed: Sep. 27, 2000

(30) Foreign Application Priority Data

Sep. 28, 1999 (JP) .......................................... 11-273810

(51) Int. Cl.[7] .............................................. A61L 15/00
(52) U.S. Cl. ......................... 602/75; 606/202; 600/485
(58) Field of Search ...................... 602/5, 75; 600/479, 600/485, 490, 493–7, 499, 500; 606/202

(56) References Cited

U.S. PATENT DOCUMENTS

| 4,653,506 A | * | 3/1987 | Romanovskaya | ........... | 128/677 |
| 4,850,369 A | * | 7/1989 | Yamasawa | ................... | 128/686 |
| 5,840,037 A | * | 11/1998 | Tochikubo et al. | ......... | 600/499 |

FOREIGN PATENT DOCUMENTS

| DE | 26 35 059 A | 2/1978 |
| FR | 2 207 683 A | 6/1974 |
| JP | 62-6804 | 1/1987 |
| JP | 8-10233 | 1/1996 |

\* cited by examiner

Primary Examiner—Nicholas D. Lucchesi
Assistant Examiner—Lalita M. Hamilton
(74) Attorney, Agent, or Firm—Morrison & Foerster, LLP

(57) ABSTRACT

There is provided a compression device for living being, simply structured and capable of fitting a site to be measured of any size. The compression device includes an elastic plate formed in one piece and elastically holding a predetermined curvature, provided for preventing a fluid bag from expanding outwards. The elastic plate includes a first curvature substantially matching a lateral cross section of a thin site to be measured, a second curvature and a connection connecting the first and second curvatures together. The connection allows the second curvature to be arranged outwardly of a virtual extension of the first curvature substantially matching the lateral cross section of the thin site to be measured. The second curvature extends inwardly of a virtual extension of the connection extending toward the second curvature.

12 Claims, 11 Drawing Sheets

COMPRESSION DEVICE FOR LIVING BEING

BACKGROUND OF THE INVENTION

1. Field of the Invention

The present invention relates to compression devices for living being, wound around a wrist, an upper arm, or a similar site to be measured, to exert pressure thereon for measuring blood pressure.

2. Description of the Background Art

A conventional compression device for living being of the above type is such as shown in FIG. 7. Compression device 30 for living being is formed of an outer cloth 31 and an inner cloth 32 together forming a belt-like bag, an air bag 33 provided internal to the belt-like bag, and an elastic curved plate 34 arranged outwardly of air bag 33 to prevent air bag 33 from expanding outwards, and also elastically holding a predetermined curvature. Outer cloth 31 and inner cloth 32 are provided with hook and loop fasteners 35 and 36, respectively, for fastening device 30 wound around a site to be measured.

A site to be measured significantly varies in size from individual to individual and for example some people have a thin wrist and other people have a thick wrist and there can be a significant difference therebetween. In the conventional compression device 30 is crucial the shape of elastic curved plate 34: If elastic curved plate 34 previously adapted to fit a thick site to be measured is used on a thin site to be measured a gap is formed therebetween and there does not build a force to hold the site to be measured and to fill the gap air bag 33 needs to further expand. As such, elastic curved plate 34 is typically adapted to fit a thin site to be measured.

In doing so, if elastic curved plate 34 is adapted to have a length corresponding to the circumference of an elliptic, thin site to be measured (wrist) 20, as shown in FIG. 8, elastic curved plate 34 fits along site to be measured 20. If this elastic curved plate 34 is applied to a person having a thick site to be measured 20, as shown in FIG. 9, elastic curved plate 34 would have an end 30b readily ingrowing into site to be measured 20 and thus causing pain to the person wearing the device. This pain increases if site to be measured 20 is thicker.

If elastic curved plate 34 is adapted to fit a thin site to be measured (wrist) and also have a length corresponding to half the circumference of an elliptic site to be measured 20, as shown in FIG. 10 (see its state before use), a person with a thin site to be measured 20 would wear the device with elastic curved plate 34 fitting site to be measured 20, as appropriate. However, if a person with a thick site to be measured 20 would wear the device then elastic curved plate 34 at an end 30a in particular exerts a force acting in a direction causing elastic curved plate 34 to come off, as shown in FIG. 11. As such, elastic curved plate 34 readily comes off site to be measured 20. Thus there does not occur a force to hold site to be measured 20 and device 30 can hardly be wound around site to be measured 20 closely.

As described above, elastic curved plate 34 adapted to fit a thin site to be measured 20 has the disadvantages as described above when it is applied on a thick site to be measured 20, and it is thus difficult to apply compression device 30 for living being to sites to be measured 20 of different sizes, as appropriate. Consequently, if device 30 is used with a sphygmomanometer mounted thereon the sphygmomanometer cannot provide a reliable blood pressure measurement.

To overcome this disadvantage, there has been developed an arm band having a bag in the form of a band with an air bag fixed thereto which spirally curves with a plurality of radii of curvature increasing from one side thereof with the air bag fixed thereto toward the remaining portion of the bag and also is elastically deformable, as disclosed in Japanese Utility Model Laying-Open No. 62-6804. With this structure, when it is applied on a thick site to be measured it does not have an end ingrowing into the site to be measured. However, the radius of curvature gradually increased prevents the band from exerting force enhanced to sufficiently grip the thick site to be measured when the band is applied on the thick site to be measured. This prevents the band from temporarily holding the site to be measured closely. As such, the band wound around the site to be measured readily moves, often resulting in inaccurate blood pressure measurement.

To overcome this disadvantage, there has been proposed an arm band using a hinge to allow a curvature corresponding to a superior arc and a curvature corresponding to an inferior arc to have a clamping force, as disclosed in Japanese Patent Laying-Open No. 8-10233. With this method, the arm band applied on a thick site to be measured can exert force enhanced to sufficiently grip the thick site to be measured. However, the hinge is provided in the form of a spring plate or the like and this increases the number of components and the number of fabrication steps and hence the manufacturing cost and it also prevents the arm band from having a simple structure in design.

SUMMARY OF THE INVENTION

The present invention contemplates a compression device for living being, simply structured and fitting a site to be measured of any size.

The present invention in one aspect provides compression device for living being, including a fluid bag internal to the compression device, expanding and contracting when the fluid bag receives and discharges fluid, respectively, and an elastic plate formed in one piece and provided internal to the compression device, arranged outwardly of the fluid bag to prevent the fluid bag from expanding outwards, and also elastically holding a predetermined curvature, the elastic plate including a first curvature substantially matching a lateral cross section of a thin site to be measured, a second curvature and a connection connecting the first and second curvatures together, the connection allowing the second curvature to be arranged outwardly of a virtual extension of the first curvature substantially matching the lateral cross section of the thin site to be measured, the second curvature extending inwardly of a virtual extension of the connection extending toward the second curvature.

In this device the elastic plate has the first curvature formed to substantially match a lateral cross section of a thin site to be measured. As such, when the device is applied on a thin site to be measured the device fits the site to be measured closely. In addition, the elastic plate has the second curvature arranged outward by means of the connection and also extending inward from the connection. As such, when the device is applied on a thick site to be measured, (1) a portion of the first curvature closer to an end of the first curvature, (2) a portion of the first curvature adjacent to the center of the first curvature and closer to the connection and (3) an end of the second curvature, a total of three points act to exert force to clamp the site to be measured in three directions. As such, the elastic plate holds the site to be measured with large force and the compression device does not ingrow into the site to be measured and thus fits the site to be measured closely.

It should be noted that in the present description a site to be measured refers to a wrist, an upper arm or a similar site. If a wrist is to be measured, then a thin site to be measured means a wrist having its entire circumference of no more than approximately 16.5 cm. If an upper arm is to be measured, then a thin site to be measured means an upper arm having its entire circumference of no more than approximately 23 cm. A thick site to be measured for a wrist corresponds to no less than approximately 18.5 cm and that for an upper arm corresponds to no less than approximately 27 cm. The virtual extension of the connection curving as seen in lateral cross section means a curvature corresponding to an extension approximating to the curvature of the connection, and the virtual extension of the connection formed in a straight line means an extension of the straight line.

The present invention in one aspect provides the compression device for living being, wherein the second curvature is desirably more distant inward from the virtual extension of the connection as the second curvature extends farther away from the connection.

Thus, the second curvature is bent at the connection inward at a large angle. As such, when the compression device is applied on a thick site to be measured, it can exert force toward the center of the site to be measured as seen in cross section. Thus, it can exert force enhanced to sufficiently grip the site to be measured to facilitate temporarily holding the site to be measured, as appropriate.

The present invention in one aspect provides the compression device for living being, wherein when applied on a thick site to be measured the second curvature has a portion in contact with the thick site to be measured by at least a predetermined length to prevent the second curvature from having an end ingrowing into the thick site to be measured.

Since the second curvature has a portion of at least a predetermined length contacting the site to be measured, it does not ingrow into the site to be measured to prick the site to be measured. This ensures a further sufficient level of force gripping the site to be measured.

The present invention in one aspect provides the compression device for living being, wherein the first curvature is formed of a center, a portion of the first curvature adjacent to the center and closer to an end of the first curvature and a portion of the first curvature adjacent to the center and closer to the connection, and when applied on a thin site to be measured the portion of the first curvature closer to the end of the first curvature and the portion of the first curvature closer to the connection cooperate to produce elasticity toward a center of the thin site to be measured, as seen in lateral cross section, to clamp the thin site to be measured.

As such, the first curvature is sufficient to exert force to sufficiently grip a thin site to be measured in applying the compression device on the thin site to be measured. As such, while the second curvature and the connection are prevented from ingrowing into a thick site to be measured, there can be created force enhanced to sufficiently grip the thick site to be measured. Note that while the first curvature is formed to substantially match a lateral cross section of a thin site to be measured, between the elastic plate and the site to be measured there is located an air bag or the like and understandably the first curvature at an intermediate portion thereof provides an widened receiving angle and with elasticity created the compression device is applied on the thin site to be measured.

The present invention in one aspect provides a compression device for living being, wherein when applied on a thick site to be measured, the first curvature elastically deforms to widen an angle formed by the portion of the first curvature closer to the end of the first curvature, the center and the portion of the first curvature closer to the connection, and receiving the site to be measured, and the second curvature contacts the thick site to be measured and elastically deforms to widen an angle formed by the connection and the second curvature with a second connection located therebetween to connect the second curvature and the connection together, to create force exerted in a direction from a surface of the thick site to be measured toward the center of the thick site to be measured, as seen in cross section.

The portion of the first curvature closer to the end of the first curvature and that of the first curvature closer to the connection cooperating to clamp the aforementioned branch point, and the second curvature can create force to grip a site to be measured in three directions. The second curvature exerts force directed toward the center of the site to be measured to prevent the end from ingrowing into the site to be measured.

The present invention in a second aspect provides a compression device for living being, including a fluid bag internal to the compression device, expanding and contracting when the fluid bag receives and discharges fluid, respectively, and an elastic plate formed in one piece and provided internal to the compression device, arranged outwardly of the fluid bag to prevent the fluid bag from expanding outwards, and also elastically holding a predetermined curvature, the elastic plate including a first curvature substantially matching a lateral cross section of a thin site to be measured, a second curvature and a connection connecting the first and second curvatures together, the connection as seen in cross section being either one of a linear connection provided in a straight line and an arcuate connection including a curvature concave outward.

Providing the connection formed as described above can reduce the circumference of the second curvature and accordingly increase the circumference of the first curvature and also increase the gradient at which the second curvature extends from the connection inwards. As such, when the compression device is applied on a thick site to be measured, the force that the second curvature exerts on a surface of the thick site to be measured can be directed to the center of the site to be measured. Furthermore, the arcuate connection having an arcuate portion concave outward and the linear connection allow the second curvature to have a higher level of elasticity for restoration than a connection having only an arcuate portion convex outward. As such, not only can the force exerted to grip a site to be measured be directed to the center of the site to be measured but it can also be increased in magnitude.

The present invention in the second aspect provides the compression device for living being, wherein the first curvature is arranged along at least half of an entire circumference of the lateral cross section of the thin site to be measured. Furthermore, the first curvature is arranged along at least 70% of an entire circumference of the lateral cross section of the thin site to be measured.

Configuring the connection as described above can increase the circumference of the first curvature. As such the first curvature is sufficient to exert force enhanced to sufficiently grip and thus fit a thin site to be measured closely.

Furthermore, if the compression device is applied on a thick site to be measured, the first curvature, with an intermediate portion thereof spaced from the thick site to be measured by at least a predetermined distance, can clamp the thick site to be measured. As such, it is not necessary for the intermediate portion of the first curvature to approach the site to be measured to significantly increase the site to be measured receiving angle to result in the intermediate portion of the first curvature exceeding its limit of elasticity. As such, the compression device can exert force enhanced to sufficiently grip the thick site to be measured easily and thus obtain durability to be used repeatedly. Such strong gripping force and durability as above can be obtained by arranging the first curvature along at least 50% of the circumference of the thin site to be measured. Furthermore to ensure such effects the first curvature desirably has a length along at least 70% of the circumferential of the thin site to be measured.

The present invention in the second aspect provides the compression device for living being, wherein the first curvature includes both ends clamping the site to be measured and a center located between the both ends and larger in thickness than the both ends.

The center increased in thickness can provide increased elasticity when the site to be measured receiving angle is widened. As such there can be provided an increased level of elasticity for restoration clamping the site to be measured.

The present invention in the second aspect provides the compression device for living being, wherein when applied on a thick site to be measured the second curvature has a portion of at least a predetermined length exerting force directed from a surface of the thick site to be measured toward a center of the thick site to be measured as seen in lateral cross section.

As such, when the compression device is applied on the thick site to be measured the second curvature does not have an end thereof ingrowing into the thick site to be measured and also cooperates with the first curvature to create a level of force that can sufficiently grip the site to be measured.

The present invention in a third aspect provides the compression device for living being, including a fluid bag internal to the compression device, expanding and contracting when the fluid bag receives and discharges fluid, respectively, and an elastic plate formed in one piece and provided internal to the compression device, arranged outwardly of the fluid bag to prevent the fluid bag from expanding outwards, and also elastically holding a predetermined curvature, the elastic plate including a first curvature substantially matching a lateral cross section of a thin site to be measured, a second curvature and a connection connecting the first and second curvatures together, when applied on a thick site to be measured the second curvature extending along a surface of the thick site to be measured and cooperating with the first curvature to create force to hold the thick site to be measured.

As such, the second curvature does not have an end thereof ingrowing into the site to be measured, while it can exert elasticity for restoration toward the center of the site to be measured as seen in lateral direction and also cooperate with the first curvature to create force enhanced to sufficiently grip the site to be measured.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

The embodiments of the present invention will now be described with reference to the drawings.

First Embodiment

Figure 1:
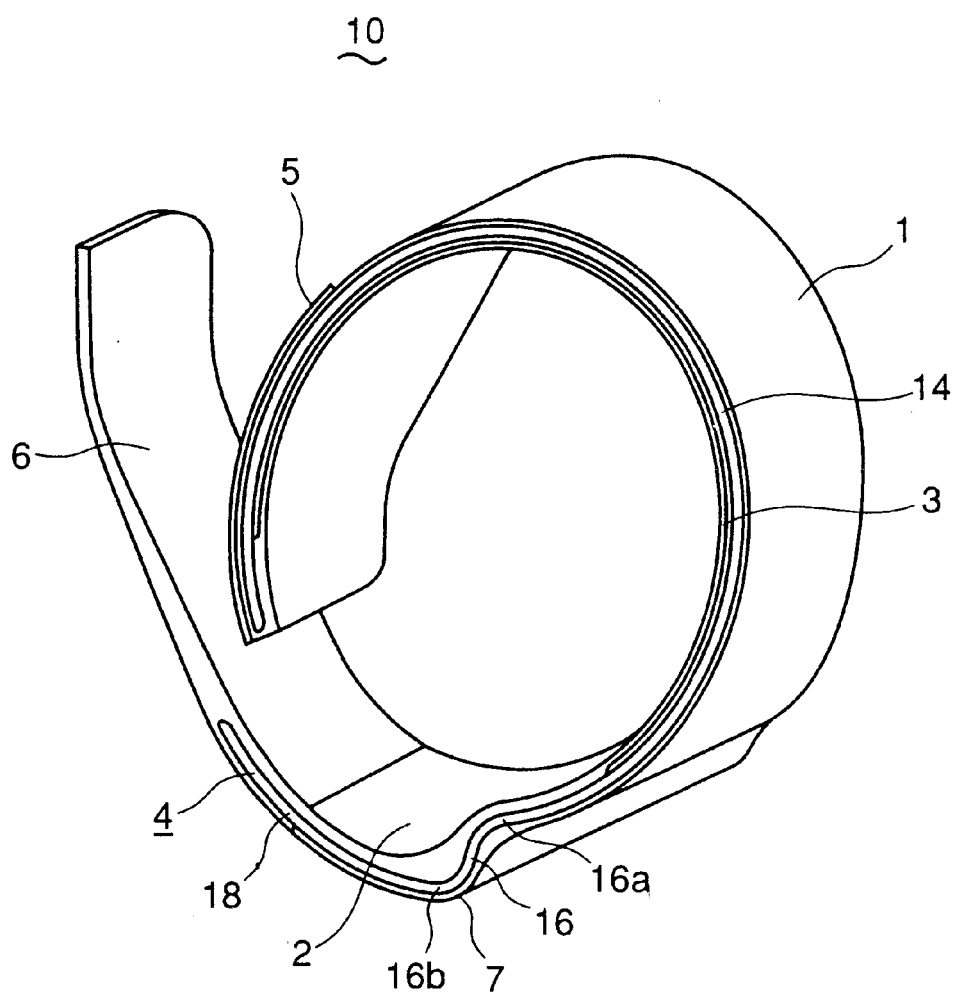
FIG. 1 is a perspective view of a compression device for living being in a first embodiment of the present invention.

As shown in FIG. 1, a compression device 10 for living being is formed of an outer cloth 1 and an inner cloth 2 together forming a belt-like bag, an air or fluid bag 3 provided internal to the belt-like bag, and an elastic curved plate or elastic plate 4 arranged outwardly of air bag 3 to prevent air bag 3 from expanding outwards, and also elastically holding a predetermined curvature. In the present embodiment the compression device is adapted to be applied on a wrist and the elastic curved plate thus has an elliptical lateral cross section matching a lateral cross section of the wrist. As has been described previously, for a thin wrist its circumference corresponds to at most approximately 16.5 cm and for a thick wrist its circumference corresponds to at least approximately 18.5 cm. Outer cloth 1 and inner cloth 2 are provided with hook and loop fasteners 5 and 6, respectively, for fastening device 10 wound around a site to be measured. This configuration is basically similar to that of the conventional device 30.

Device 10 is characterized in that elastic curved plate 4 is formed of a first curvature 14 substantially matching a lateral cross section of a thin site to be measured, a second curvature 18 and a connection 16 connecting the first and second curvatures together. Connection 16 is continuous from the first curvature 14 via a first connection 16a and continuous to the second curvature 18 via a second connection 16b. Connection 16 and a portion of the second curvature 18 together form a deformation 7 raised outward. Elastic curved plate 4 is arranged along an outer side of air bag 3 and herein has both ends extending further than those of air bag 3. Deformation 7, i.e., connection 16 and a portion of the second curvature 18 are provided in elastic curved plate 4 in a vicinity of end 10c, which corresponds to an end pulled by a portion including a hook and loop fastener when the device is applied on a site to be measured, and at deformation 7 device 10 is raised slightly outwards, although the shape of deformation 7 and the length of elastic curved plate 4 that are shown in the figures are merely illustrative and they may be changed as appropriate.

Figure 3:
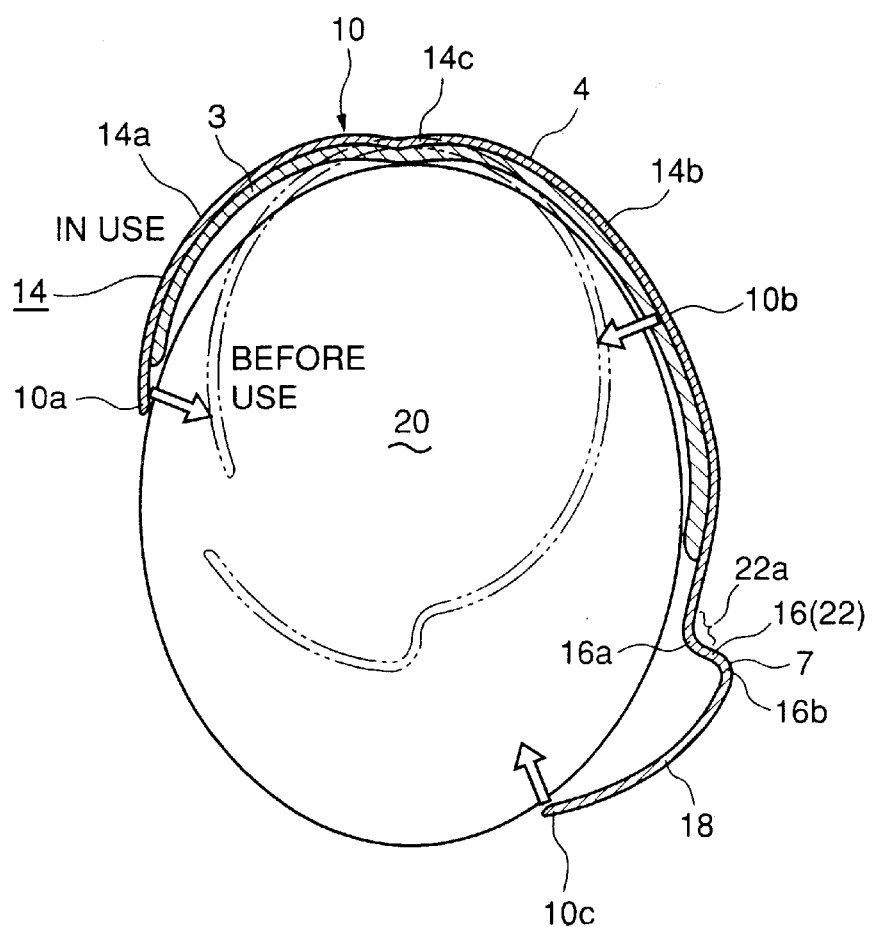
FIG. 3 is a schematic cross section of the device (the elastic curved plate) of the embodiment applied on a thick site to be measured.

In FIG. 3, the connection in a vicinity of the first connection 16a has an outwardly concave, arcuate portion as seen in lateral cross section. In the present embodiment, the connection corresponds to an arcuate connection including an arcuate portion having its center of curvature positioned outward. As such, the elastic curved plate can be enhanced in elasticity for restoration. Furthermore, the second curvature 18, reduced in length, can be significantly angled inwards from connection 16. Thus, the second curvature can contact the site to be measured and thus grip the site to be measured with force exerted toward the center of the site to be measured as seen in lateral cross section. While the above elastic curved plate is provided by molding organic resin in one piece, it may be formed of any flexible, elastic material.

Figure 2:
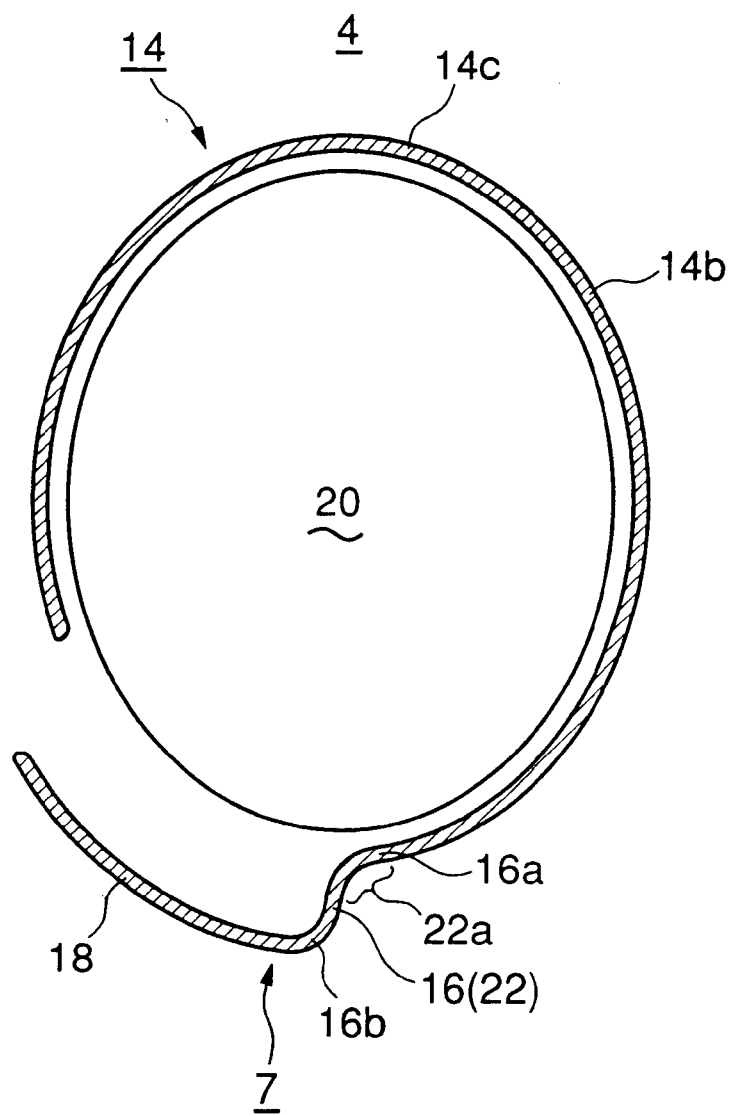
FIG. 2 is a schematic cross section of the device (an elastic curved plate) of the embodiment applied on a thin site to be measured.

Elastic curved plate 4 is formed to substantially match a lateral cross section (e.g., an ellipse of FIG. 2 or 3) of a thin site to be measured, and, as shown in FIG. 2, it has a length substantially corresponding to the circumference of site to be measured 20 when device 10 is wound around the thin site to be measured, with the second curvature 18 positioned in the ellipse of site to be measured 20 substantially at one end of the longer diameter.

When compression device 10 for living being thus configured is applied on a person having a thin site to be measured, elastic curved plate 4, having the first curvature 14 originally formed to substantially match a lateral cross section of a thin site to be measured, can fit site to be measured 20 to wind device 10 around site to be measured 20 closely. As shown in FIG. 2, the first curvature 14 is configured of a center 14c and a portion of the first curvature 14a adjacent to center 14c and closer to an end of the first curvature 14 and a portion of the first curvature 14b adjacent to center 14c and closer to the connection. When elastic curved plate 4 is wound around closely, as described above, members 14a and 14b form an angle receiving a site to be measured that is slightly increased to closely clamp a thin site to be measured.

In contrast, for a person having a thick site to be measured, as shown in FIG. 3, elastic curved plate 4 has the first curvature 14 flexing outward. As a result, the first curvature's end 10a, an intermediate portion 10b of the first curvature closer to the connection, and the second curvature's end 10c for a total of three points exert force clamping site to be measured 20 in three directions. In FIG. 3, it is important that the above three points each act to provide force gripping the site to be measured in a direction toward the center of the site to be measured as seen in lateral cross section. For example, if the second curvature's end 10c exerts force to grip the site to be measured upper leftward as seen in FIG. 3, then the device would insufficiently, temporarily attached and it would move and come off when the band is wound around. This often results in inaccurate blood pressure measurement.

Thus, elastic curved plate 4 can have an increased force holding site to be measured 20 and device 10 can thus fit the site to be measured closely. Thus, device 10 can fit sites to be measured of different sizes, as appropriate. As such, if device 10 is applied to a sphygmomanometer the sphygmomanometer can provide a more reliable blood pressure measurement.

Furthermore, as shown in FIG. 3, while elastic curved plate 4 is formed to match a geometry of a thin site to be measured, connection 16 allows the second curvature 18 to be offset outwardly of the first, virtual curvature matching the thin site to be measured. As such, end 10c hardly ingrows into the site to be measured. Furthermore, the second curvature 18 can extend inwardly of a virtual extension of connection 16 and it is farther away as it further extends therefrom. As such, it can contact a thick site to be measured and thus exert force to grip the thick site to be measured toward the center thereof as seen in lateral cross section. As such, it cooperates with other portions to act to firmly clasp site to be measured 20. Thus the person subjected to the measurement does not feel pain while the clip plate can reliably hold the site to be measured.

Figure 4:
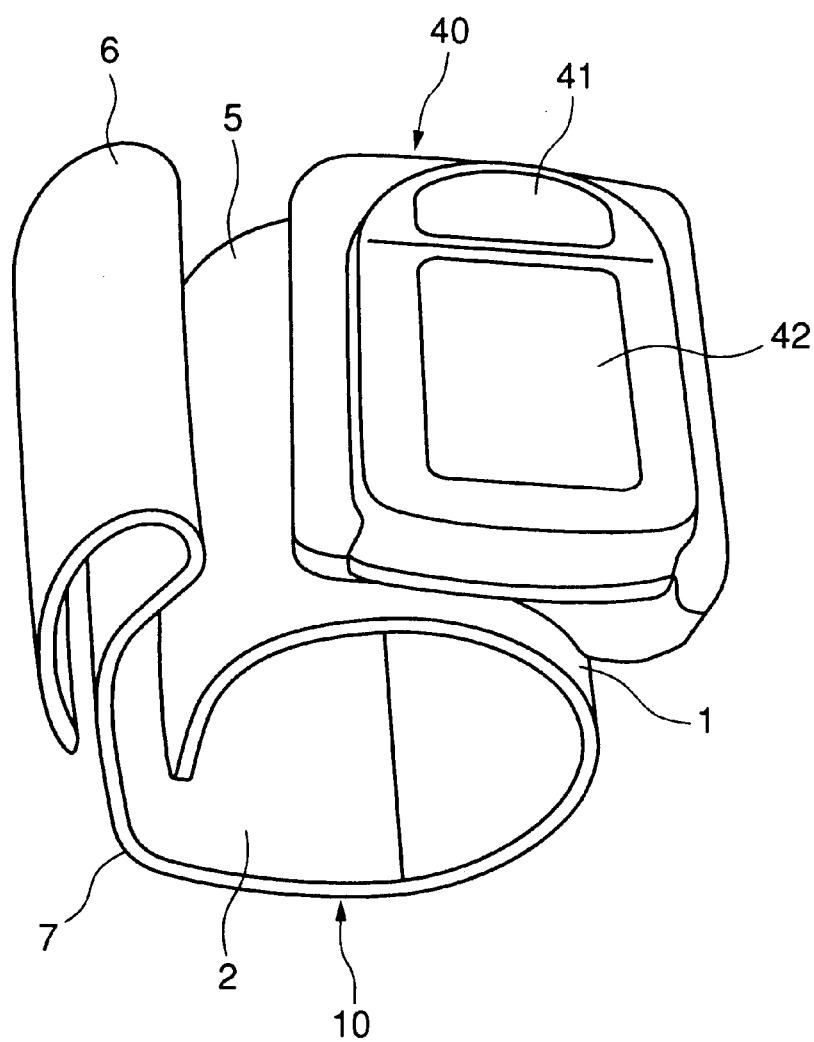
FIG. 4 is a perspective view of an example of the compression device of the embodiment in use with a sphygmomanometer.

FIG. 4 shows an example of the present compression device 10 for living being in use with a sphygmomanometer. This sphygmomanometer is used on a wrist, and it includes a body 40, with the compression device 10 detachably attached thereto. Body 40 includes an operation unit 41 configured of a measurement starting button and the like and a display unit 42 for displaying highest and lowest blood pressure values.

Second Embodiment

Figure 5:
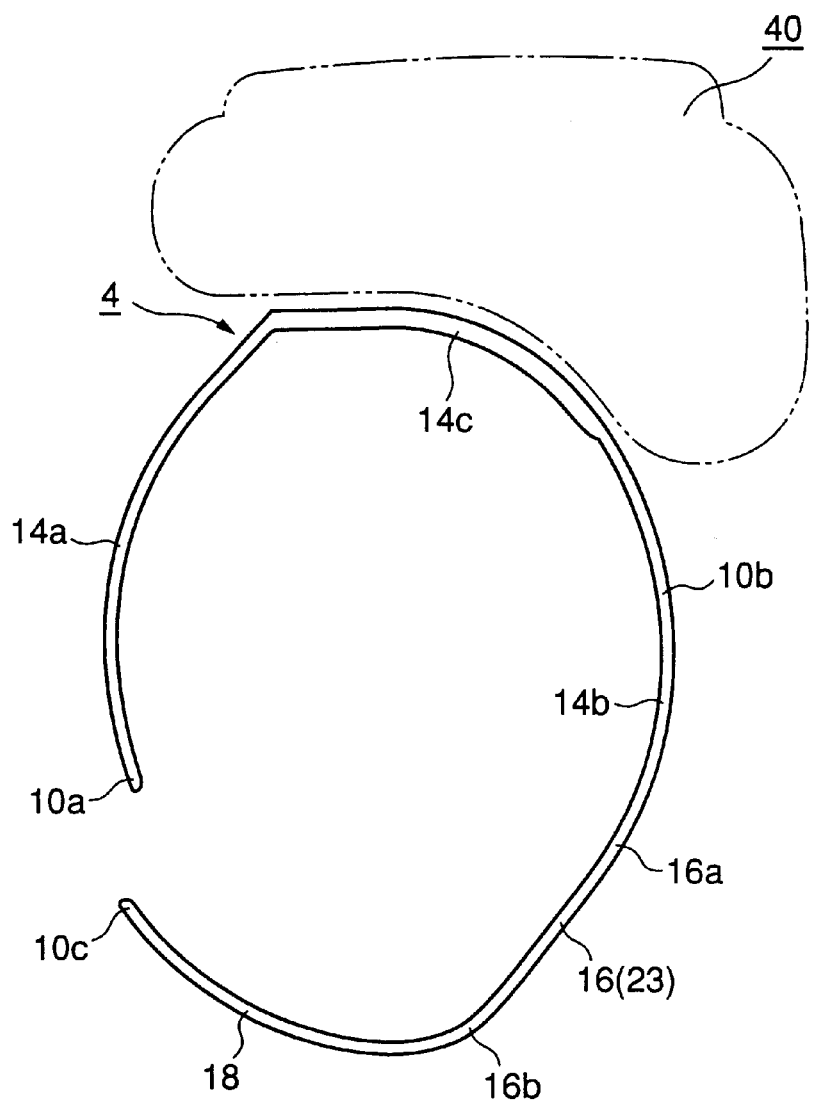
FIG. 5 is a cross section of an elastic curved plate of a compression device for living being in a second embodiment of the present invention.

FIG. 5 shows a lateral cross section of elastic curved plate 4 in a second embodiment of the present invention. Elastic curved plate 4 is formed of a first curvature 14, a second curvature 34 and a connection 24 connecting the first and second curvatures together. The first and second curvatures are each an elliptical, arcuate portion as seen in lateral cross section. The first curvature 14 is sectionalized into a portion of the first curvature 10a closer to an end of the first curvature, a portion of the first curvature 14b closer to the connection, and a center 14c located therebetween. The first curvature 14 is adapted to substantially match a lateral cross section of a thin site to be measured. Center 14c is formed thick as seen in cross section to provide further increased elasticity for restoration clamping the site to be measured. The second embodiment is distinguished from the first embodiment in that the first curvature 14 and the second curvature 34 are connected together by connection 34 provided in the form of a straight line as seen in lateral cross section. This straight line contacts both of an elliptical arc of the first curvature and that of the second curvature.

Although not as well as in the first embodiment, forming the connection linearly as seen in cross section also allows the second curvature, reduced in length, to be angled significantly inwardly of a virtual extension of the connection. Furthermore, although not as much as the elasticity for restoration of an arcuate connection having an arcuate portion concave outward, the elasticity for restoration around the present connection can also be enhanced when the second curvature warps outward and contacts a site to be measured. The second curvature angled inward can contact the site to be measured to exert force toward the center of the site to be measured to grip the site to be measured and the second curvature can thus cooperate with the other portions to temporarily hold the site to be measured with a large gripping force. The present embodiment is distinguished from the first embodiment in that the second curvature is slightly increased in length and a portion thereof closer to the connection than the end thus contacts a site to be measured. This can readily prevent the end from ingrowing into and prick a significantly thick site to be measured.

Third Embodiment

Figure 6A:
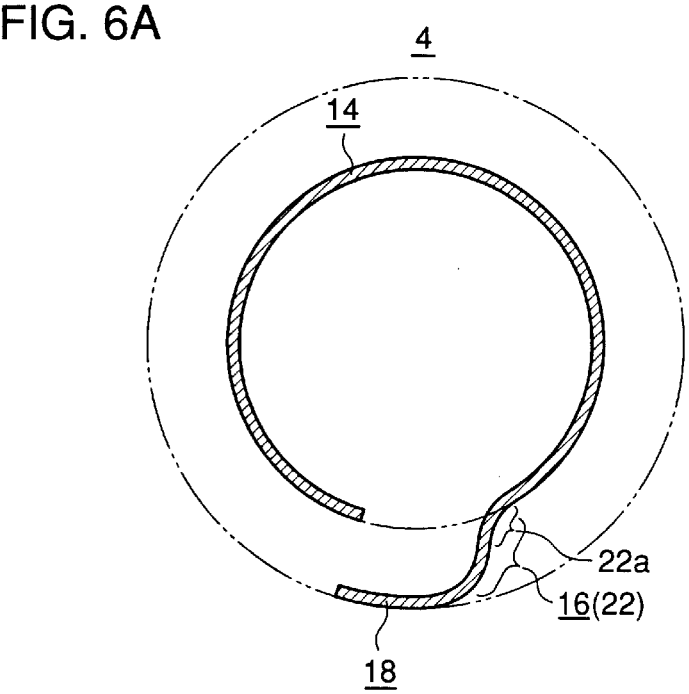
FIGS. 6A and 6B are cross sections of an elastic curved plate of a compression device for living being in a third embodiment of the present invention, with an arcuate connection including an arc concave outward, as shown in FIG. 6A, and with a linear connection in contact with a first curvature and a second curvature, as shown in FIG. 6B.
Figure 6B:
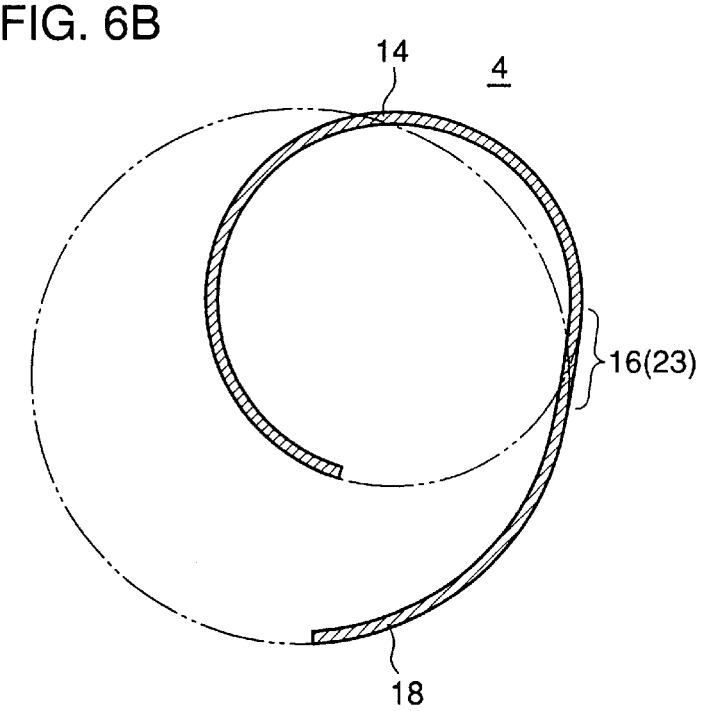
Figure 7:
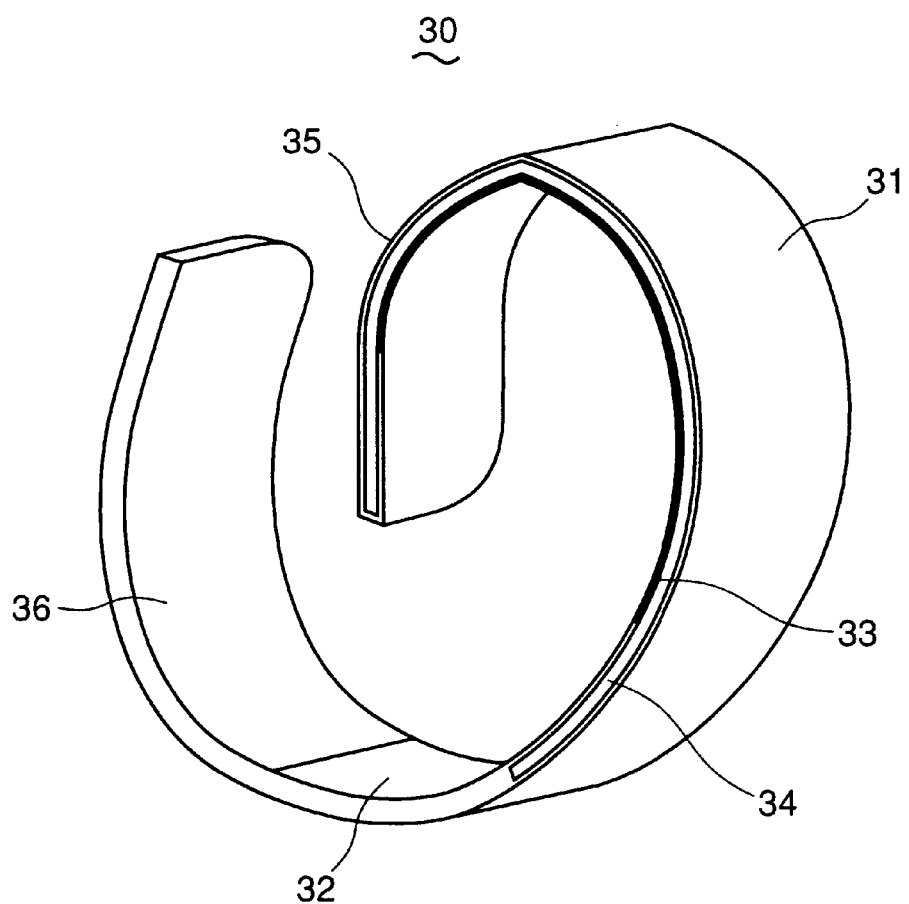
FIG. 7 is a perspective view of an example of a conventional compression device for living being.
Figure 8:
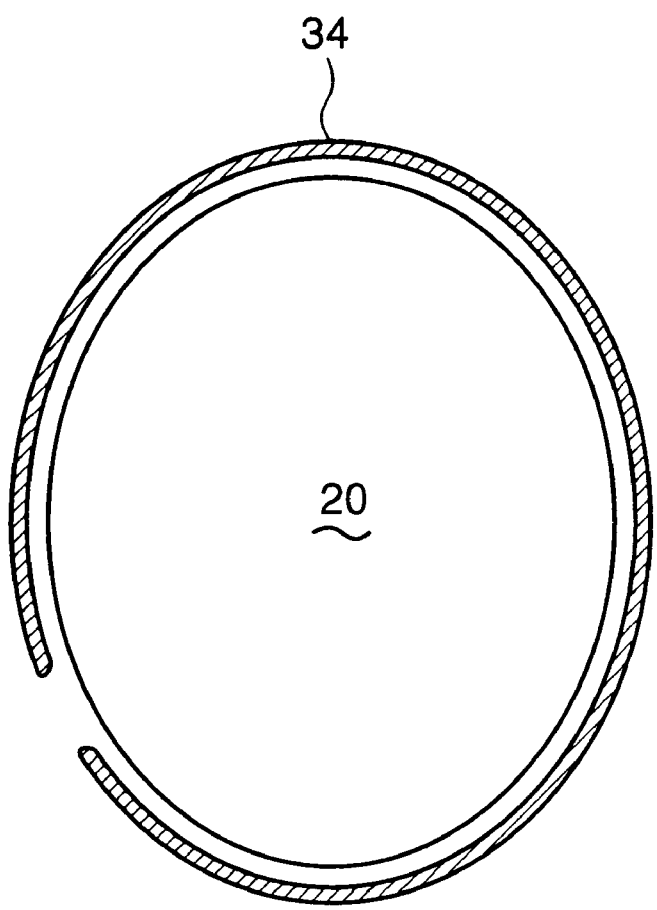
FIG. 8 is a schematic cross section of a conventional compression device (an elastic curved plate) adapted for a thin site to be measured when the device is applied on a thin site to be measured.
Figure 9:
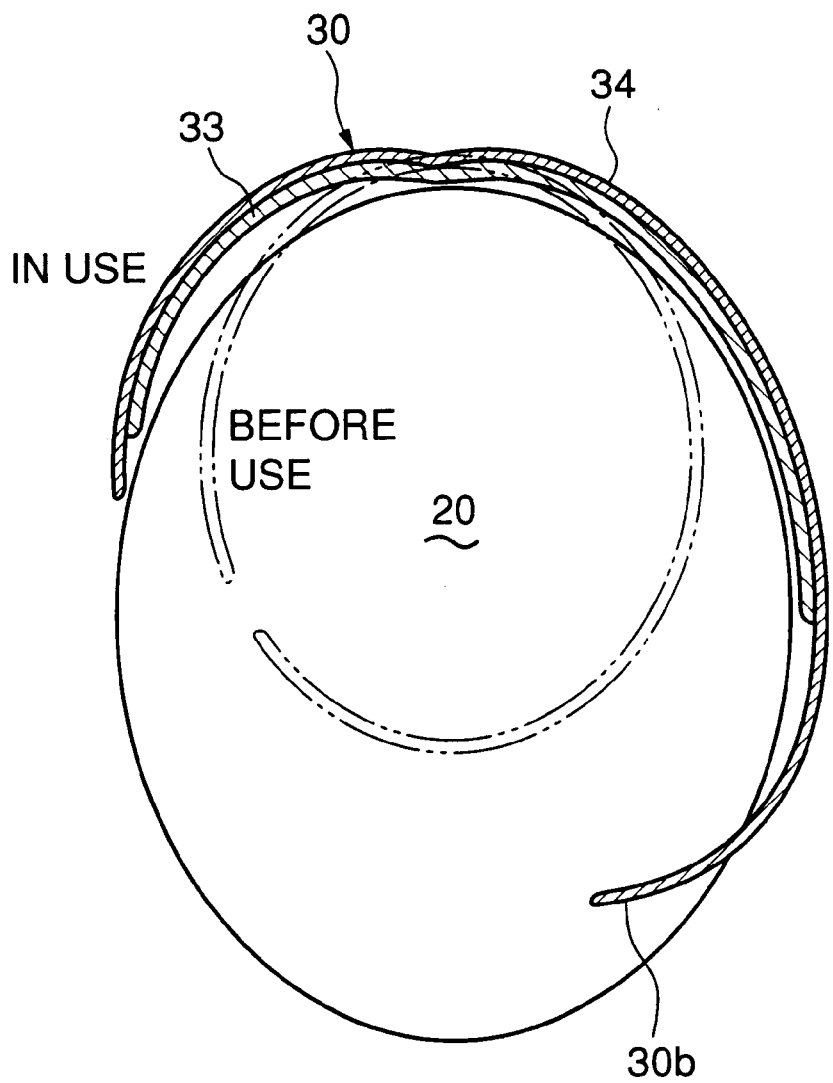
FIG. 9 is a schematic cross section of the conventional compression device (the elastic curved plate) adapted for a thin site to be measured when the device is applied on a thick site to be measured.
Figure 10:
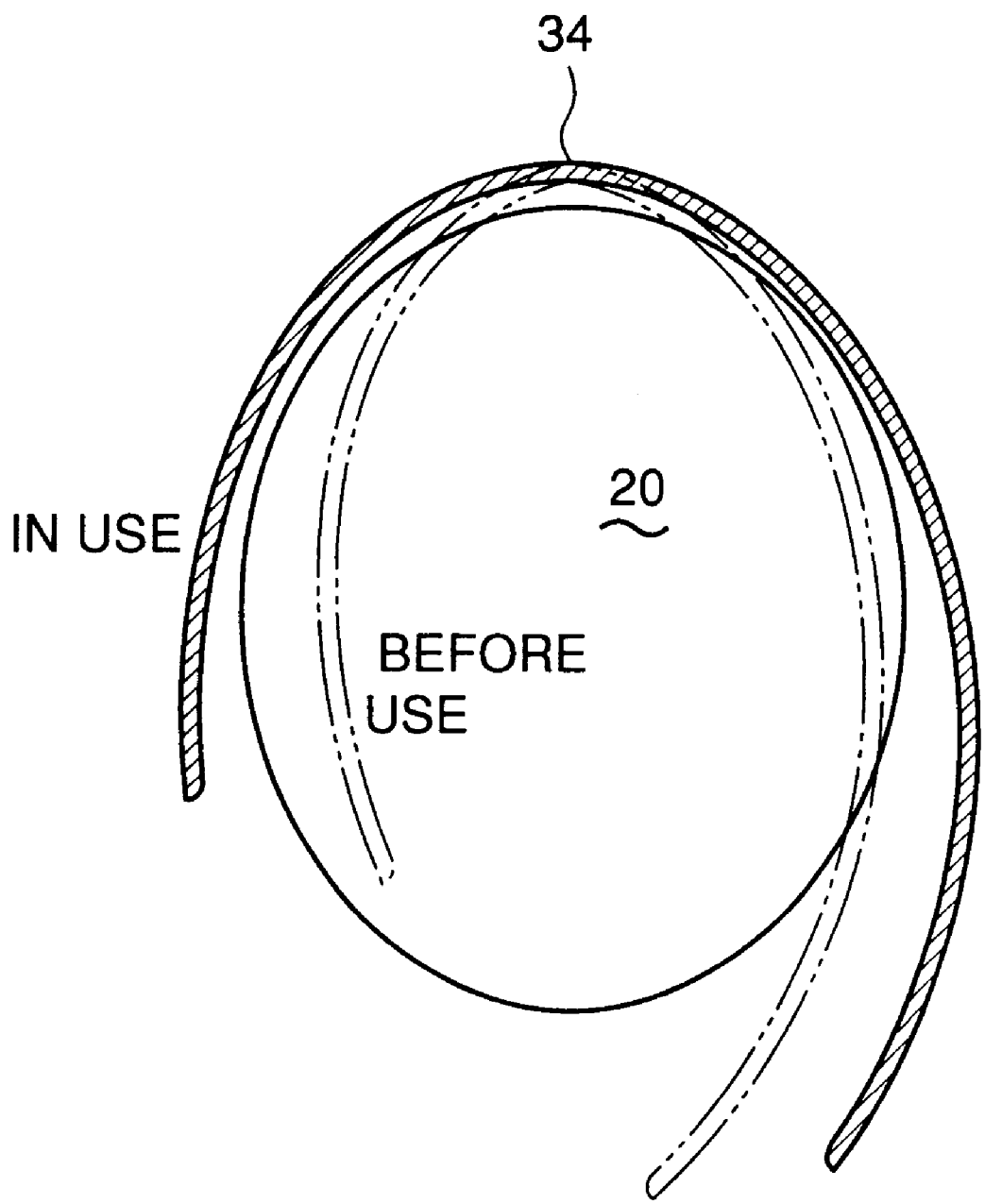
FIG. 10 is a schematic cross section of a another conventional compression device (an elastic curved plate) adapted for a thin site to be measured when the device is applied on a thin site to be measured.
Figure 11:
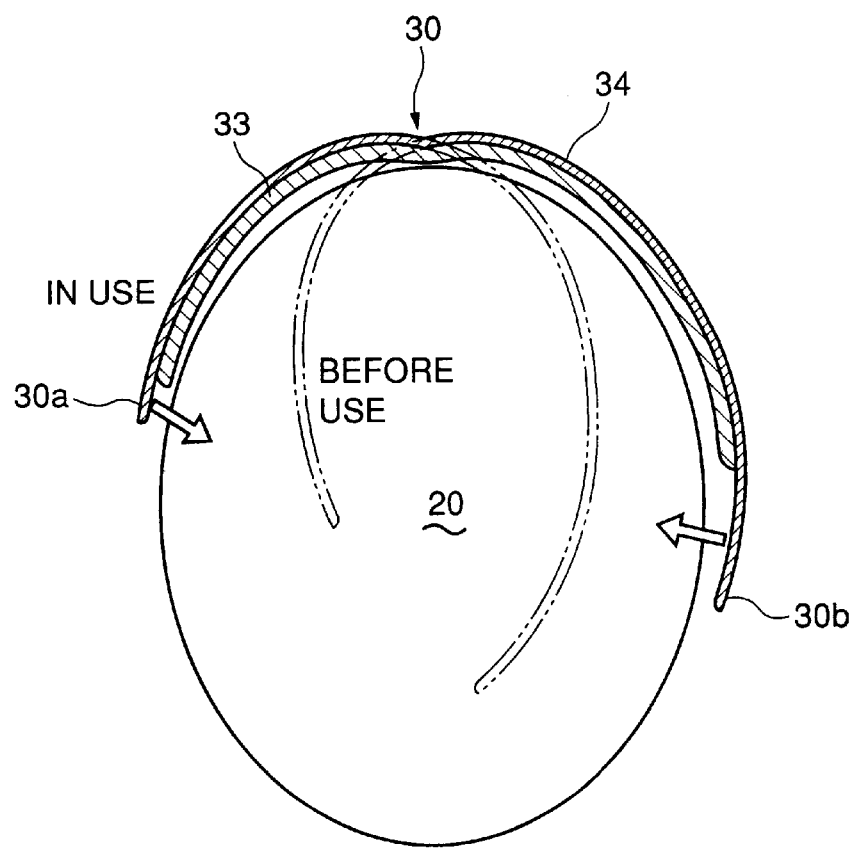
FIG. 11 is a schematic cross section of another conventional compression device (the elastic curved plate) adapted for a thin site to be measured when the device is applied on a thick site to be measured.

FIGS. 6A and 6B are schematic cross sections of an elastic curved plate of a compression device for living being in a third embodiment of the present invention, applied on an upper arm. FIG. 6A is a schematic cross section of a connection corresponding to an arcuate connection including an arcuate portion concave outward, and FIG. 6B is a schematic cross section of a connection provided as a linear connection formed in a straight line. In the present embodiment, the elastic curved plate has a geometry determined to allow the same to be wound around an upper arm. While a wrist is elliptical as seen in cross section, an upper arm is round in lateral cross section. As such, the elastic curved plate has the first curvature formed to substantially match a lateral cross section of a thin site to be measured. As has been described previously, for an upper arm a thin site to be measured has a circumference of at most approximately 23 cm and a thick site to be measured has a circumference of at least approximately 27 cm. The present elastic curved plate can be provided when a site to be measured in the first and second embodiments is changed to have a round lateral cross section and a thin site to be measured or a thick site to be measured has a circumference ranged as above.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A compression device for living being, comprising a fluid bag internal to said compression device, expanding and contracting when said fluid bag receives and discharges fluid, respectively, and an elastic plate formed in one piece and provided internal to said compression device, arranged outwardly of said fluid bag to prevent said fluid bag from expanding outwards, and also elastically holding a predetermined curvature, said elastic plate including a first curvature substantially matching a lateral cross section of a thin site to be measured, a second curvature and a connection connecting said first and second curvatures together, said connection allowing said second curvature to be arranged outwardly of a virtual extension of said first curvature substantially matching the lateral cross section of said thin site to be measured, said second curvature extending inwardly of a virtual extension of said connection extending toward said second curvature, wherein said connection is an arcuate connection having a curvature concave outward.

2. The compression device of claim 1, wherein said second curvature is more distant inward from the virtual extension of said connection as said second curvature extends farther away from said connection.

3. The compression device of claim 1, wherein when applied on a thick site to be measured said second curvature has a portion in contact with the thick site to be measured by at least a predetermined length to prevent said second curvature from having an end ingrowing into the thick site to be measured.

4. The compression device of claim 1, wherein said first curvature has a connection segment attached to said connection connecting said first and second curvatures together, said first curvature has an end segment opposite said connection segment on said first curvature, and said first curvature has a center segment positioned between said connection segment and said end segment.

5. The compression device of claim 4, wherein a first portion of said first curvature between said connection segment and said center segment cooperate with a second portion of said first curvature between said end segment and said center segment to elastically deform to clamp a thin site to measured.

6. The compression device of claim 4, wherein when said compression device is attached to a thick site to be measured:

said first curvature elastically deforms to widen an angle formed by said first portion and said second portion;

said connection has two portions, a first connection portion and a second connection portion, wherein said second curvature is connected to said second connection portion of said connection;

said second curvature contacts said thick site to be measured, wherein said second curvature deforms to widen an angle between said first connection, and said second connection portion exerts a force in a direction toward said thick site to be measured.

7. A compression device for living being, comprising a fluid bag internal to said compression device, expanding and contracting when said fluid bag receives and discharges fluid, respectively, and an elastic plate formed in one piece and provided internal to said compression device, arranged outwardly of said fluid bag to prevent said fluid bag from expanding outwards, and also elastically holding a predetermined curvature, said elastic plate including a first curvature substantially matching a lateral cross section of a thin site to be measured, a second curvature and a connection connecting said first and second curvatures together, when applied on a thick site to be measured said second curvature extending along a surface of the thick site to be measured and cooperating with said first curvature to create force to hold the thick site to be measured, wherein said connection is an arcuate connection having a curvature concave outward.

8. A compression device for a living being, comprising:

a fluid bag internal to said compression device, wherein said fluid bag expands and contracts when said fluid bag receives and discharges fluid respectively;

a one piece elastic plate positioned internal to said compression device and outwardly of said fluid bag, wherein said elastic plate prevents said fluid bag from expanding outward and said elastic plate elastically holds a predetermined shape;

said predetermined shape includes a first curvature substantially matching a lateral cross section of a first site to be measured, a second curvature, and a connection connecting said first and second curvatures together, wherein said connection is an arcuate connection having a curvature concave outward.

9. The compression device of claim 8, wherein said first curvature is arranged along at least half of an entire circumference of the lateral cross section of said thin site to be measured.

10. The compression device of claim 8, wherein said first curvature is arranged along at least 70% of an entire circumference of the lateral cross section of said thin site to be measured.

11. The compression device of claim 8, wherein said first curvature includes both ends clamping said site to be measured and a center located between said both ends and larger in thickness than said both ends.

12. The compression device of claim 8, wherein when applied on a thick site to be measured said second curvature has a portion of at least a predetermined length exerting force directed from a surface of the thick site to be measured toward a center of the thick site to be measured as seen in lateral cross section.

* * * * *